(12) United States Patent
Torii

(10) Patent No.: US 10,426,422 B2
(45) Date of Patent: Oct. 1, 2019

(54) RADIOGRAPHIC APPARATUS, RADIOGRAPHIC SYSTEM, RADIOGRAPHIC METHOD, AND STORAGE MEDIUM

(71) Applicant: CANON KABUSHIKI KAISHA, Tokyo (JP)

(72) Inventor: Sota Torii, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 195 days.

(21) Appl. No.: 15/684,640

(22) Filed: Aug. 23, 2017

(65) Prior Publication Data

US 2018/0055473 A1 Mar. 1, 2018

(30) Foreign Application Priority Data

Aug. 30, 2016 (JP) ................................. 2016-167776

(51) Int. Cl.
*A61B 6/00* (2006.01)
*H04N 5/32* (2006.01)
*H04N 5/369* (2011.01)
*H04N 5/353* (2011.01)

(52) U.S. Cl.
CPC ............. *A61B 6/527* (2013.01); *A61B 6/542* (2013.01); *H04N 5/32* (2013.01); *H04N 5/3535* (2013.01); *H04N 5/3696* (2013.01); *A61B 6/503* (2013.01)

(58) Field of Classification Search
CPC ......... A61B 6/503; A61B 6/527; A61B 6/542; H04N 5/32; H04N 5/3535; H04N 5/3696
See application file for complete search history.

(56) References Cited

U.S. PATENT DOCUMENTS

| | | | | |
|---|---|---|---|---|
| 7,340,034 | B2* | 3/2008 | Hayashida | A61B 6/00 378/98 |
| 2005/0129176 | A1* | 6/2005 | Kokubun | A61B 6/503 378/95 |
| 2013/0077749 | A1* | 3/2013 | Akahori | A61B 6/486 378/62 |
| 2013/0274539 | A1* | 10/2013 | Yamada | A61N 5/1039 600/1 |
| 2015/0189194 | A1* | 7/2015 | Tajima | A61B 6/488 378/62 |

FOREIGN PATENT DOCUMENTS

JP 05084237 A * 4/1993
JP 2007-82907 A 4/2007

* cited by examiner

*Primary Examiner* — Marcus H Taningco
(74) *Attorney, Agent, or Firm* — Canon U.S.A., Inc. IP Division

(57) ABSTRACT

To quickly detect body movement during radiography and provide a radiographic image less affected by the body movement, a radiographic apparatus includes a detection unit including a first pixel that detects radiation and a second pixel that detects the radiation at a frame rate higher than a frame rate of the first pixel, and a body movement detection unit that, while a subject is irradiated with the radiation, detect body movement of the subject by comparing a plurality of pieces of radiographic data detected by the second pixel with each other.

19 Claims, 9 Drawing Sheets

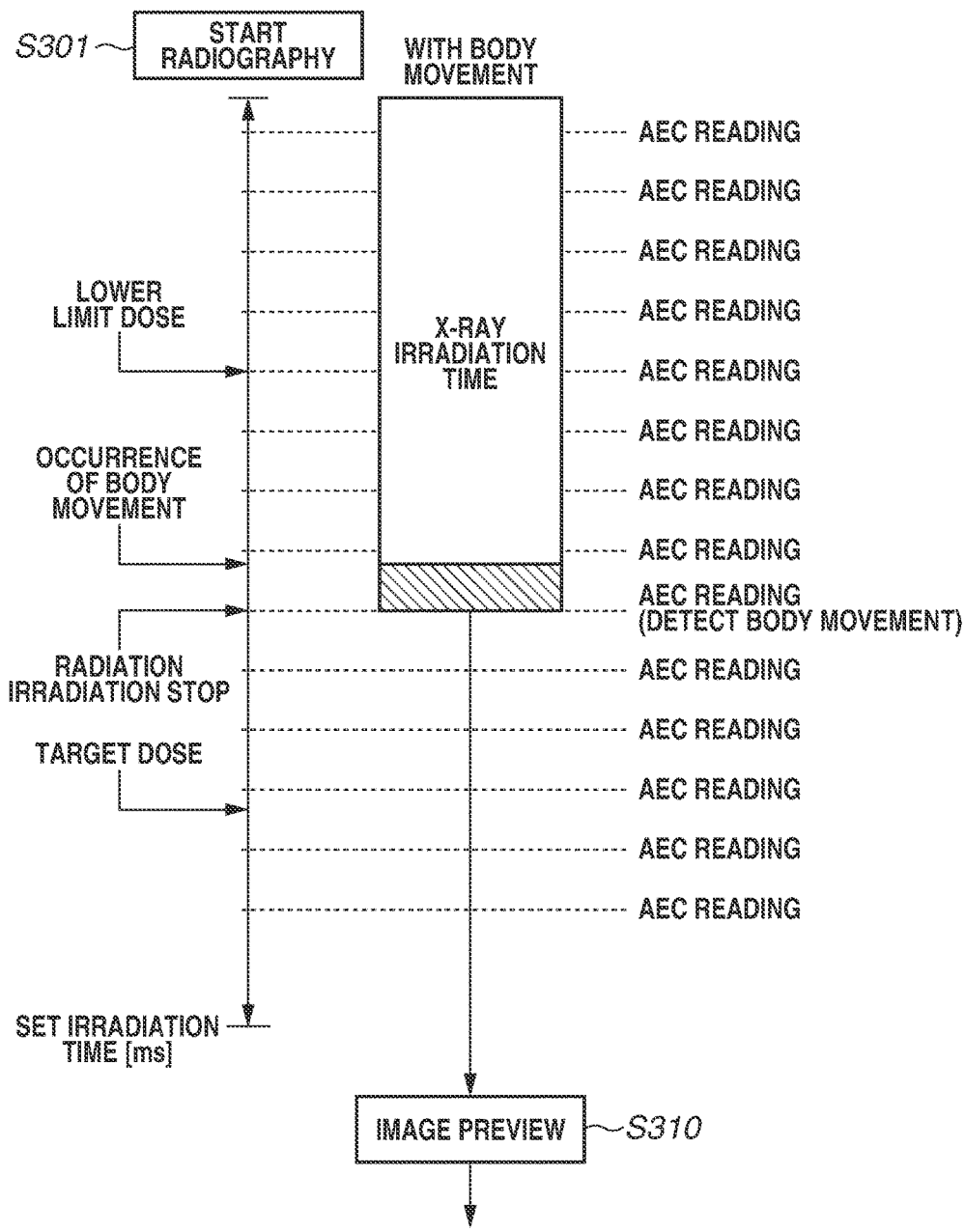

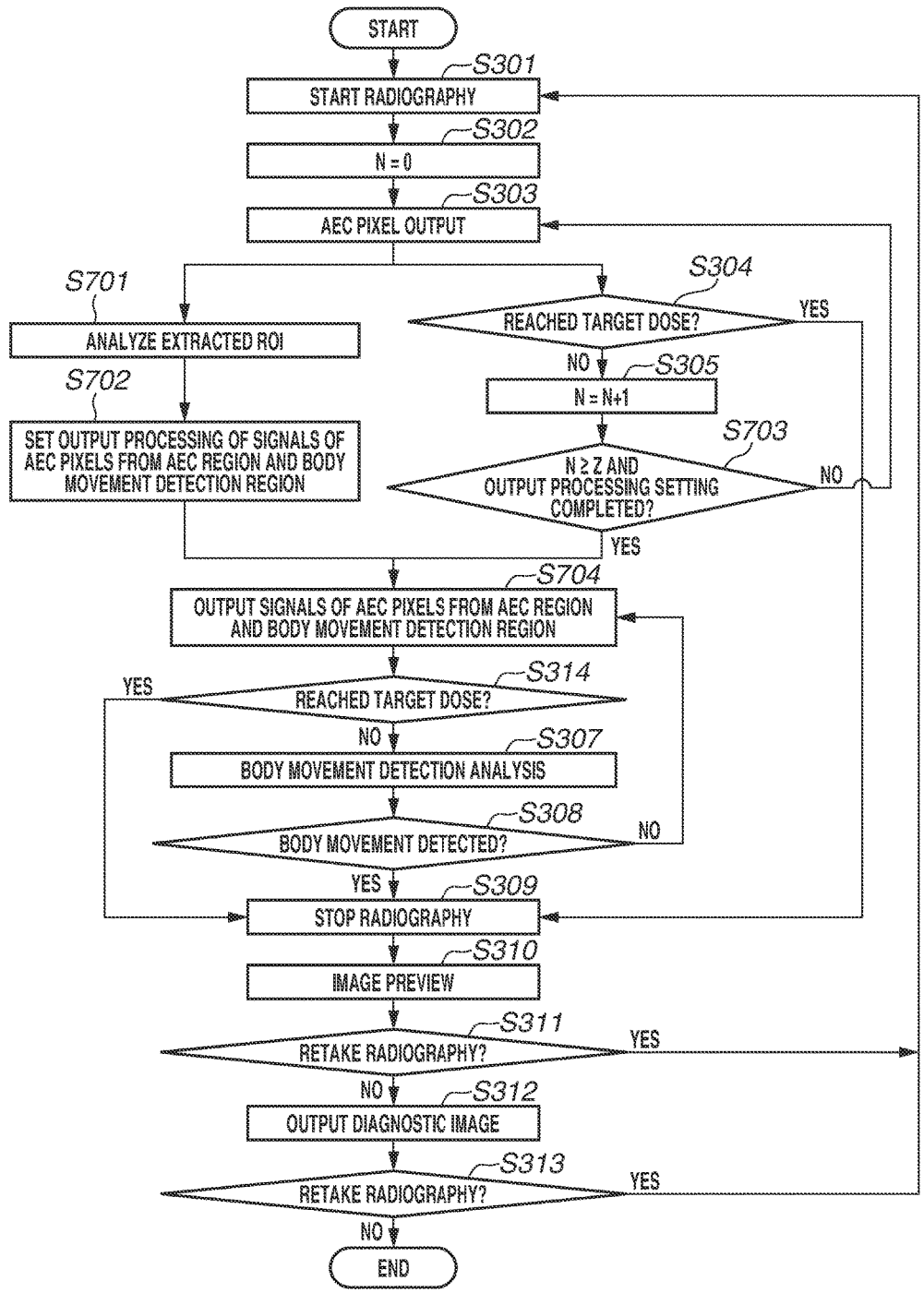

RADIOGRAPHIC APPARATUS, RADIOGRAPHIC SYSTEM, RADIOGRAPHIC METHOD, AND STORAGE MEDIUM

BACKGROUND

Field

The present disclosure relates to a radiographic apparatus, a radiographic system, a radiographic method, and a storage medium for detecting body movement of a subject when radiography is performed.

Description of the Related Art

In recent years, radiographic apparatuses that have two-dimensionally arranged solid-state image sensors using amorphous silicon or monocrystalline silicon have been put into practice. These radiographic apparatuses sometimes have issues that body movement of a subject during radiography leads to blurring in an acquired radiographic image, where the blurring results in deterioration of image quality. Body movement, in particular, often tends to appear in radiography involving a long radiation irradiation time, radiography of a region including respiratory organs and heart and lungs, and radiography of infants.

When body movement occurs, an operator observes a subject being radiographed and immediately checks an acquired radiographic image to determine whether the radiography needs to be retaken. However, the operator may fail to notice body movement in a displayed image because in many cases, a monitor in an imaging room has a limited resolution and displays a reduced radiographic image. The reduced image can be enlarged for a detailed check of body movement, but this operation lengthens an image checking time of the operator. In view of the above, a method for automatically detecting body movement based on an acquired radiographic image has been proposed. For example, Japanese Patent Application Laid-Open No. 2007-82907 discusses a technique in which a plurality of images of a subject taking the same posture is captured when a moving image is obtained and whether body movement has occurred is determined through comparison among the plurality of images. However, since the technique discussed in Japanese Patent Application Laid-Open No. 2007-82907 uses pixels for forming a radiographic image to determine whether body movement has occurred, radiography is required to be performed for a plurality of times. This means that body movement cannot be detected in real time.

SUMMARY

A radiographing apparatus that obtains a radiographic image of a subject includes a detection unit including a first pixel configured to detect radiation and a second pixel configured to detect the radiation at a frame rate higher than a frame rate of the first pixel, and a body movement detection unit configured to, while the subject is irradiated with the radiation, detect body movement of the subject by comparing a plurality of pieces of radiographic data detected by the second pixel with each other.

Further features will become apparent from the following description of exemplary embodiments with reference to the attached drawings.

BRIEF DESCRIPTION OF THE DRAWINGS

FIG. 5B is a diagram illustrating an operation of the second pixels according to the first exemplary embodiment (with body movement)

FIG. 7 is a flowchart illustrating processing executed by a radiographic apparatus according to the second exemplary embodiment.

DESCRIPTION OF THE EMBODIMENTS

Exemplary embodiments are described below with reference to the attached drawings. As the exemplary embodiments described below, the present disclosure is applied to a radiographic apparatus that performs radiographing by using X-rays as one type of radiation to obtain radiographic image data of a subject. The present disclosure is not limited to a radiographic apparatus described below, and can be applied to a radiographic apparatus that uses other types of radiation (such as α-rays, β-rays, or γ-rays, for example) to perform radiographing to obtain radiographic image data of a subject.

Figure 1:
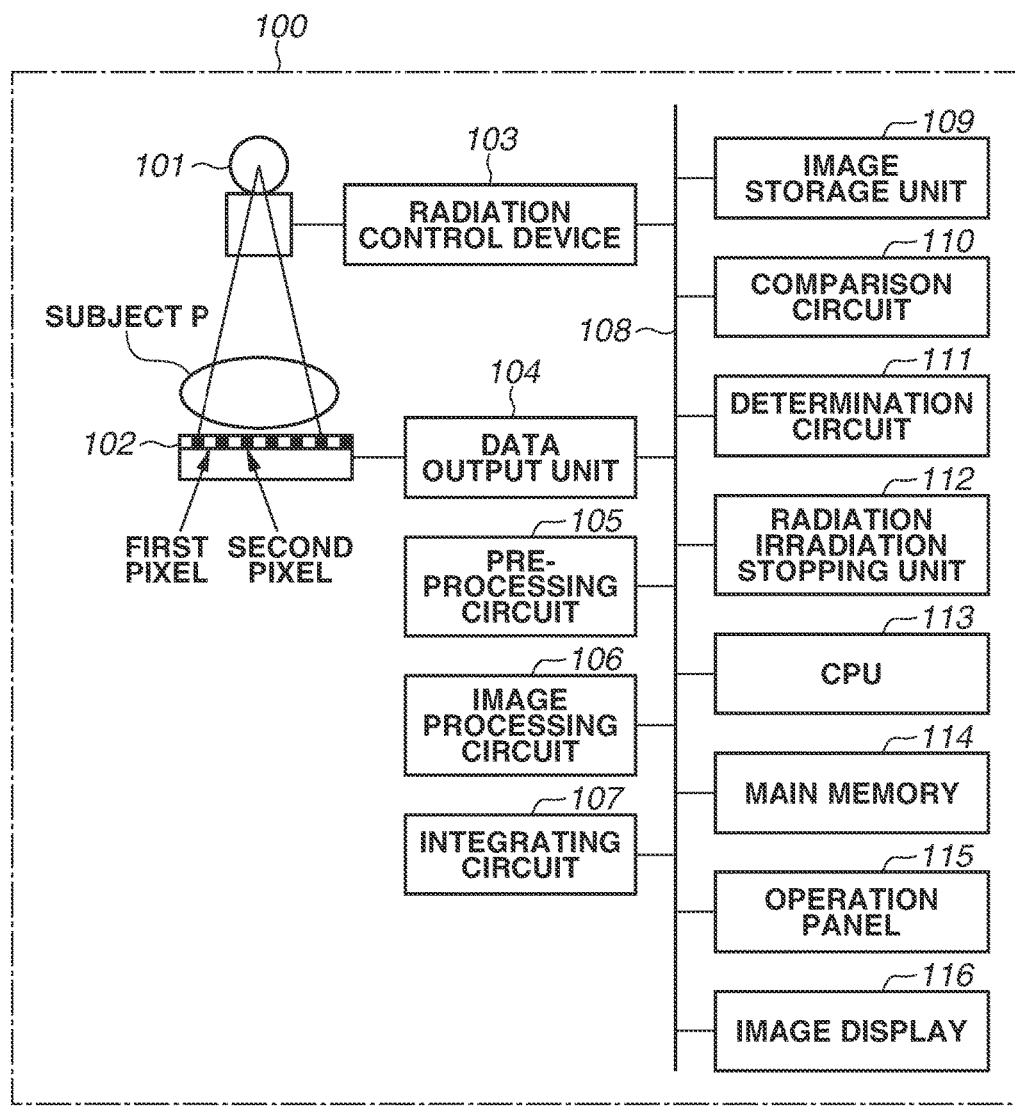
FIG. 1 is a diagram illustrating a configuration of a radiographic apparatus according to a first exemplary embodiment.

FIG. 1 is a diagram illustrating a configuration of a radiographic apparatus 100 according to a first exemplary embodiment. The radiographic apparatus 100 according to the present exemplary embodiment is particularly used for medical purposes. A radiation irradiation unit (radiation generation unit) 101 in FIG. 1 generates radiation and irradiates a subject P with the radiation.

A radiation detection unit (detection unit) 102 includes a plurality of pixels that detects the radiation. The pixels include a first pixel that outputs radiographic image data and a second pixel (Automatic Exposure Control (AEC) pixel) with which signals can be read at a frame rate higher than a frame rate of a case using the first pixel. The radiation detection unit (detection unit) 102 includes the first pixel that detects radiation, and the second pixel that detects the radiation at a frame rate higher than a frame rate of the first pixel. The first pixel outputs radiographic data for generating a radiographic image of a subject, and the second pixel outputs radiographic data for detecting body movement of the subject.

As described above, the first pixel detects radiation and outputs the radiographic image data. Thus, the first pixel is for obtaining a radiographic image. The second pixel outputs a plurality of pieces of radiographic data for detecting body movement.

The radiation detection unit 102 detects incident radiation transmitted through the subject P and generates radiographic image data. The radiation irradiation unit 101 includes a radiation generation unit, such as an X-ray tube, that generates radiation and a collimator that defines a divergence angle of a beam of the radiation generated by the radiation generation unit.

A radiation control device 103 controls a dose of the radiation emitted from the radiation irradiation unit 101. The radiation control device 103, a data output unit 104, and a pre-processing circuit 105 are connected to a central processing unit (CPU) bus 108. An image processing circuit 106, an integrating circuit 107, an image storage unit 109, a comparison circuit 110, a determination circuit 111, a radiation irradiation stopping unit 112, a CPU 113, a main memory 114, an operation panel 115, and an image display 116 are also connected to the CPU bus 108.

The main memory 114 stores various types of data or the like required for the CPU 113 to execute processing, and also functions as a working memory for the CPU 113. The CPU 113 uses the main memory 114 to perform control for, for example, processing executed by the apparatus as a whole in accordance with an operation performed on the operation panel 115. When an image capturing instruction is input through the operation panel 115 from a user, the CPU 113 transfers the image capturing instruction to the data output unit 104. Upon reception of the image capturing instruction, the data output unit 104 performs radiography by controlling the radiation irradiation unit 101 and the radiation detection unit 102.

In radiography, the radiation irradiation unit 101 irradiates the subject P with radiation, and the radiation detection unit 102 outputs a radiographic image signal. The subject P according to the present exemplary embodiment is a human body, and thus the radiation detection unit 102 outputs a radiographic image of the human body. The data output unit 104 converts the radiographic image signal output from the radiation detection unit 102 into a digital signal, and transmits the digital signal as radiographic image data to the pre-processing circuit 105.

The pre-processing circuit 105 executes pre-processing, such as offset correction processing and gain correction processing, on the radiographic image data obtained from the data output unit 104. The pre-processed radiographic image data is transferred to the main memory 114 and to the image processing circuit 106, under control of the CPU 113. The pre-processing circuit 105 or the image processing circuit 106 functions as an image forming unit, and generates a radiographic image of the subject P from radiation detected by the radiation detection unit (detection unit) 102.

Figure 2:
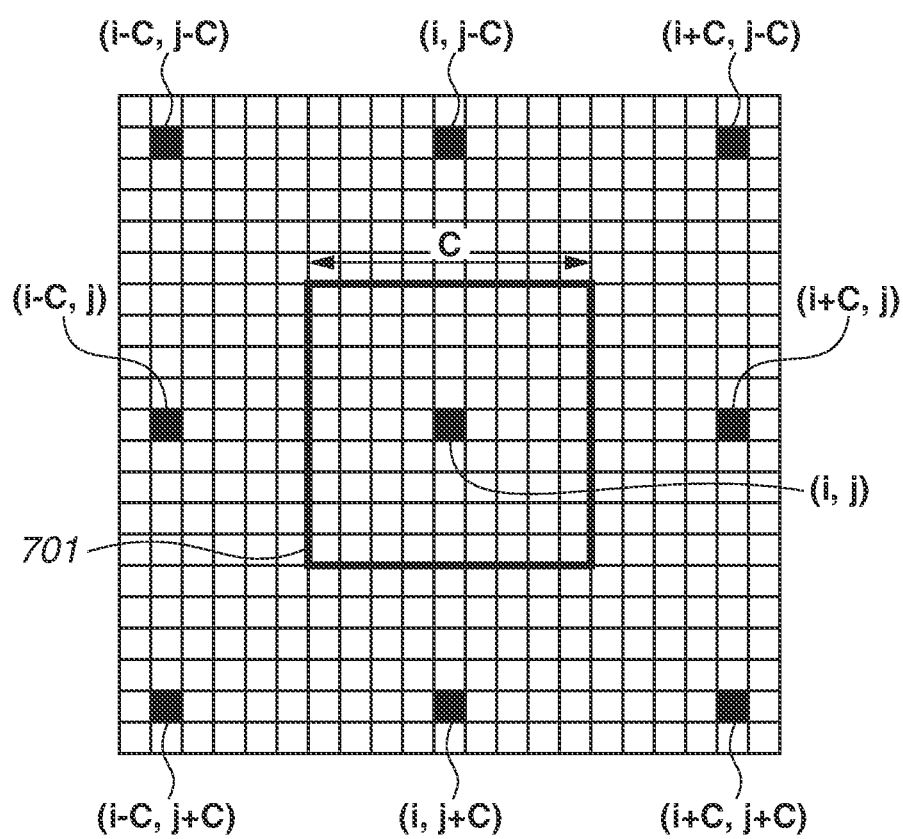
FIG. 2 is a diagram illustrating a pixel arrangement in a detection unit according to the first exemplary embodiment.

The data output unit 104 can perform conventional still image reading, and can also read radiographic image signals from the second pixels (AEC pixels) that are two-dimensionally arranged as illustrated in FIG. 2, at a frame rate higher than a frame rate of the first pixels. The pixel arrangement illustrated in FIG. 2 is merely an example, and the second pixels can be asymmetrically arranged or can be arranged in partially dense and sparse manner.

Each of a plurality of images acquired by the data output unit 104 is stored in the image storage unit 109. The plurality of stored images is compared with each other by the comparison circuit (body movement detection unit) 110 as appropriate in a manner described below. The comparison circuit (body movement detection unit) 110 compares a plurality of pieces of radiographic image data, which is detected by the second pixels while the subject P is irradiated with radiation, to detect body movement of the subject P.

The determination circuit 111 executes threshold processing based on a result of the comparison. When the determination circuit 111 detects body movement, the radiation irradiation stopping unit 112 outputs an irradiation stop signal to stop radiation irradiation by the radiation irradiation unit 101 via the radiation control device 103. Thus, the radiation irradiation stopping unit (stopping unit) 112 stops the radiation irradiation when body movement of the subject P is detected.

Figure 3:
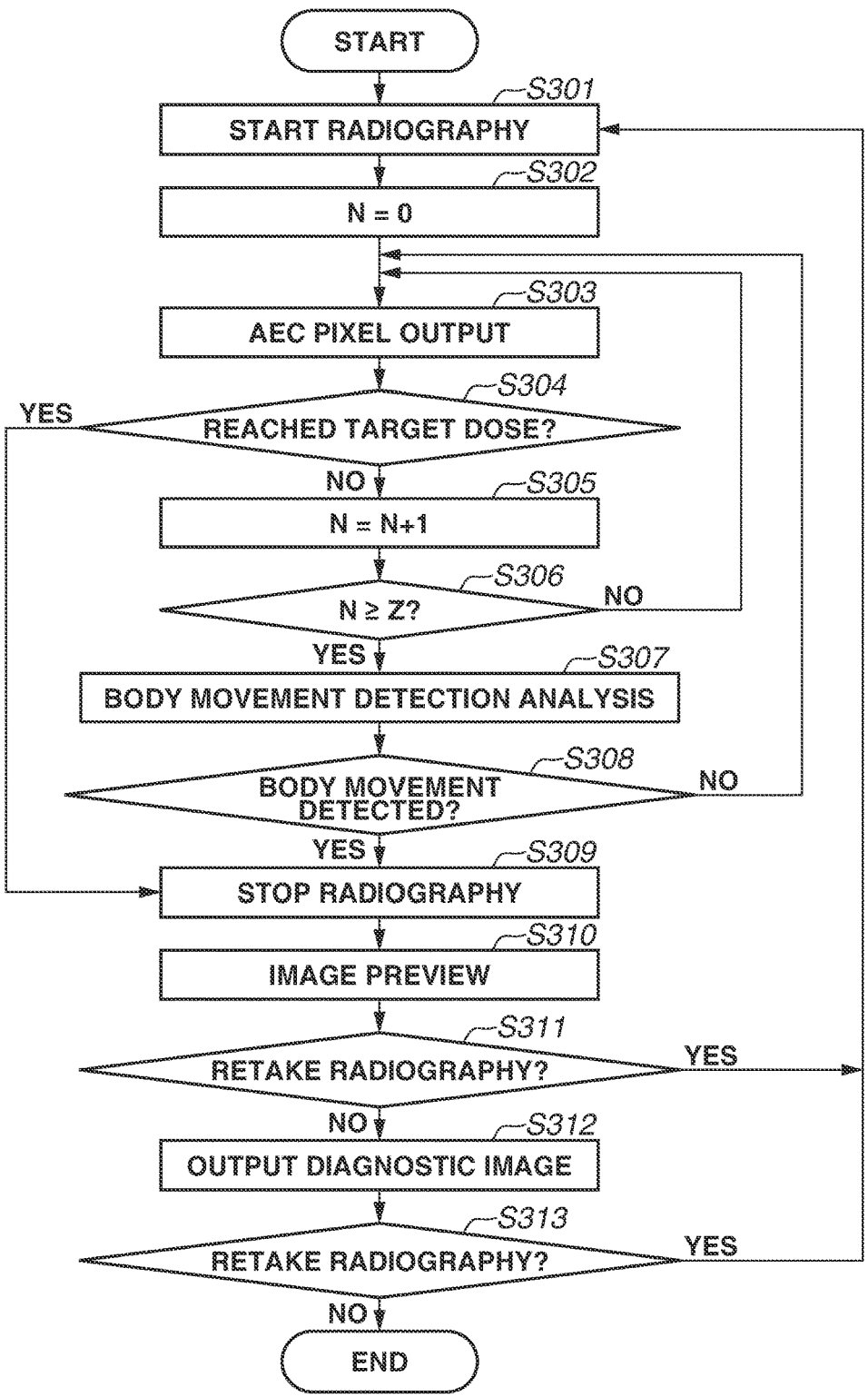
FIG. 3 is a flowchart illustrating processing executed by the radiographic apparatus according to the first exemplary embodiment.

FIG. 3 is a flowchart illustrating processing according to the present exemplary embodiment. In step S301, radiography is started. In step S302, an AEC pixel reading count (N) is initialized. In step S303, the data output unit 104 sequentially reads signals out from the AEC pixels while the radiation is being emitted. The signals read out from the AEC pixels are stored in the image storage unit 109 and are sequentially integrated by the integrating circuit 107.

In step S304, the determination circuit 111 determines whether an average value of pixel values, which are pixel values in a predetermined region, integrated by the integrating circuit 107 has reached a predetermined target dose (target value) set by the user. In a case where the value has reached the target dose, (YES in step S304), the processing proceeds to step S309. In step S309, the radiation irradiation stopping unit 112 transmits the irradiation stop signal to the radiation control device 103, and the radiography is stopped. The radiation irradiation stopping unit (stopping unit) 112 can stop the radiation irradiation, when an integrated value (sum) of the plurality of pieces of radiographic image data detected by the second pixels exceeds the predetermined target value, or when a radiation detection time of the second pixels exceeds a predetermined target time.

In a case where the average value has not reached the target dose (NO in step S304), the processing proceeds to step S305. In step S305, the AEC pixel reading count (N) is incremented. Then, in step S306, whether the AEC pixel reading count (N) has exceeded a predetermined count Z is determined. In a case where the reading count (N) is smaller than the predetermined count Z (NO in step S306), the processing proceeds to step S303 without executing body movement detection analysis.

The predetermined count Z is set as appropriate in accordance with a method of analyzing detected body movement. The predetermined count Z can be a fixed value or can be variably set by analyzing fluctuation of the average AEC pixel output. The smallest settable number of the predetermined count Z is two. However, the number can be set as a fixed value or can be variably set based on unstable AEC pixel output since AEC pixel output is unstable for first several counts when activation of the X-ray tube is unstable.

The quality of the radiation output from the X-ray tube is unstable for a time after the X-ray tube is activated. Thus, the body movement can be more accurately detected by not using AEC pixel outputs corresponding to the counts 1 to Z−1, that is, until when AEC pixel outputs is stabilized, in the body movement detection. As described below, AEC pixel output can be maintained to be stable by AEC pixel output correction.

In a case where the AEC pixel reading count (N) is greater than or equal to the predetermined count Z in step S306 (YES in step S306), the processing proceeds to step S307. In step S307, the comparison circuit 110 performs body movement detection analysis in a manner as described below. The body movement detection analysis can be performed by the pre-processing circuit 105 or by the image processing circuit 106, depending on accuracy and analysis speed of the body movement detection.

In a case where body movement is detected in steps S307 and S308 (YES in step S308), the processing proceeds to step S309. In step S309, the radiography is stopped in the manner as described in the case where the result of the determination in step S304 is YES. In the present exemplary embodiment, a message indicating that body movement has been detected is displayed on the image display 116 so that the user has a lower risk of failing to notice body movement in an image checking step described below. The detection of body movement can be notified in any manner as long as the user can recognize occurrence of body movement of the subject P. For example, a personal computer (PC) or the radiation detection unit 102 can emit sounds or the like.

In a case where body movement is not detected in steps S307 and S308 (NO in step S308), the processing returns to step S303. In the present exemplary embodiment, dose control is performed for a region of interest (ROI) by using the AEC pixels. When the dose of radiation is controlled using a timer, such as a photo timer, the processing can be forcibly terminated with a radiation irradiation stop signal output from the photo timer. The processing in steps S303 and S304 can be omitted in a case where the dose does not need to be managed.

When the radiography is stopped, the processing proceeds to step S310. In step S310, the image display 116 displays an image (preview image) on the screen so that the user can perform simple image checking. In step S311, the user checks whether body movement is noticed in the image by the image checking and determines whether to redo the radiography. In a case where no body movement is noticed and determination is made that the radiography does not need to be retaken (NO in step S311), the processing proceeds to step S312. In a case where body movement is noticed and determination is made that the radiography needs to be retaken (YES in step S311), the processing returns to step S301 to redo the radiography. In step S312, the image display 116 outputs a diagnostic image to a monitor so that the user can make a final check. In a case where the diagnostic image is determined to meet a requirement for diagnosis and determination is made that the radiography does not need to be retaken (NO in step S313), the radiographing is finished. In a case where the diagnostic image is determined to not meet a requirement for diagnosis and determination is made that the radiography needs to be retaken (YES in step S313), the processing returns to step S301 to redo the radiography.

Figure 4:
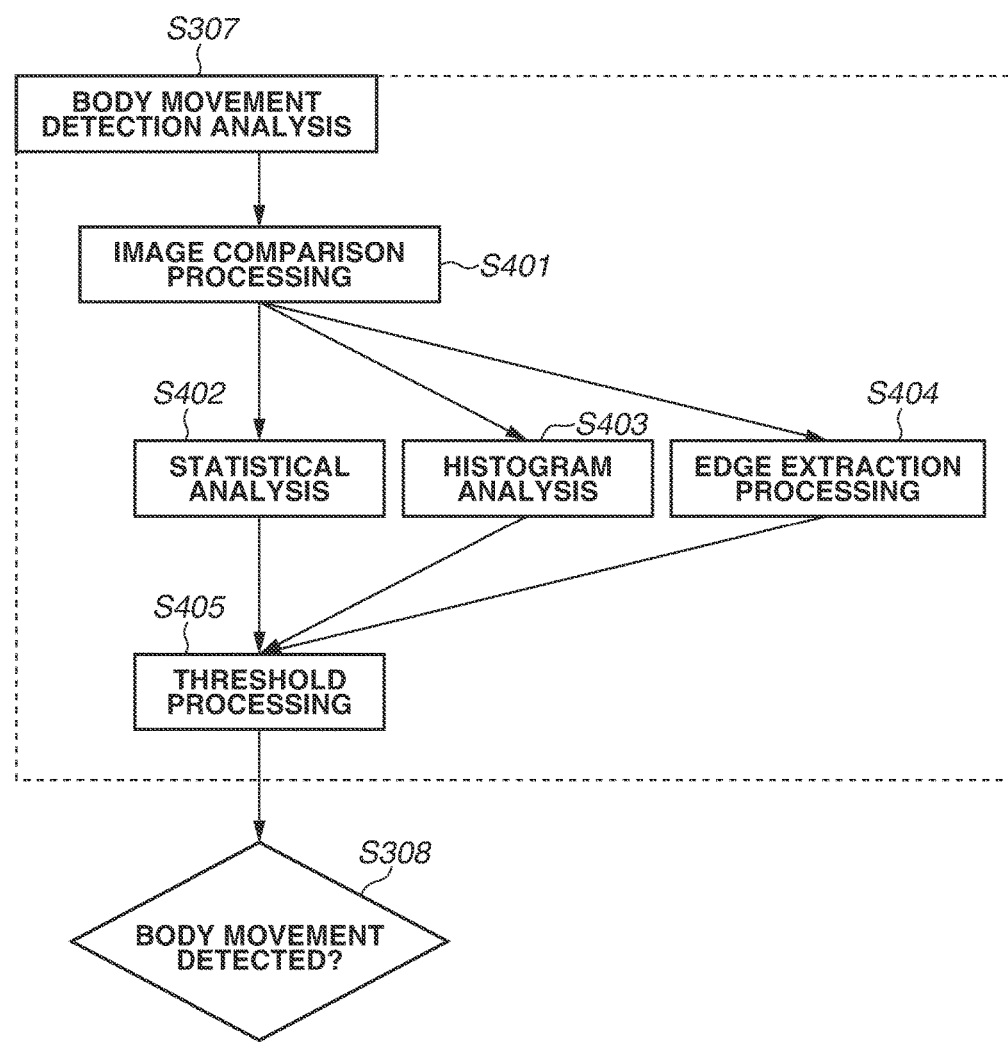
FIG. 4 is a flowchart illustrating body movement detection analysis according to the first exemplary embodiment.

FIG. 4 is a flowchart illustrating the detailed processing in step S307 in FIG. 3. The body movement detection analysis of the processing in step S307 will be described in detail.

In step S401, the AEC pixel outputs sequentially obtained at and after the count Z are compared with the AEC pixel output at the count Z−1. An AEC pixel output difference is thus acquired for each pixel. More specifically, a difference between the AEC pixel output corresponding to the count Z and the AEC pixel output corresponding to the count Z−1 is acquired for each pixel. Then, a difference between an AEC pixel output corresponding to a count Z+1 and the AEC pixel output corresponding to the count Z−1 is acquired for each pixel.

As described above, the comparison circuit (body movement detection unit) 110 detects the body movement of the subject P by comparing radiographic data (outputs from the second pixels corresponding to the counts Z and Z+1) with, as reference radiographic data, predetermined radiographic data (outputs from the second pixels corresponding to the count Z−1).

The comparison circuit (body movement detection unit) 110 determines the reference radiographic data based on the number of radiation detection counts (for example, the count Z−1) or a radiation detection time (for example, an elapsed time after the count 0) of the second pixels. The reference radiographic data can be determined based on characteristics of a stability (characteristics of activation) or fluctuation of an output from the radiation irradiation unit (radiation generation unit) 101 that generates radiation.

Correction can be performed for the activation characteristics of the X-ray tube or the fluctuation of the output from the X-ray tube, as long as predetermined analysis speed can be achieved. More specifically, before the difference is acquired, an AEC pixel output $A_{(i,j)\_N}$ corresponding to the count N can be corrected to be $AC_{(i,j)\_N}$ in a manner such that an average value $A_{ave\_N}$ of the AEC pixel outputs corresponding to the count N becomes equal to an average value $A_{ave\_Z-1}$ of the AEC pixel outputs corresponding to the count Z−1. For example, the AEC pixel output $A_{(i,j)\_N}$ corresponding to the count N is corrected to be $AC_{(i,j)\_N}$, with the following formulae (1) and (2):

$$A_{ave\_N} = \frac{1}{i \times j} \sum A_{(i,j)N}, \text{ and} \quad (1)$$

$$AC_{(i,j)\_N} = A_{(i,j)\_N} \times \frac{A_{ave\_Z-1}}{A_{ave\_N}}, \quad (2)$$

where (i,j) is coordinates of an AEC pixel and AC is an AEC pixel output after the correction.

As described above, the comparison circuit (body movement detection unit) 110 performs the correction in such a manner that the average value of the radiographic data becomes equal to the average value of the reference radiographic data. Then, the comparison circuit (body movement detection unit) 110 can compare the corrected radiographic data with the reference radiographic data to detect body movement of the subject P.

In step S402, the comparison circuit (body movement detection unit) 110 performs statistical analysis on output images acquired by the processing in step S401. The statistical analysis in step S402 is performed for each portion or region, similarly to a standard deviation or an average value of the image. The detection target herein is body movement, and calculation of the standard deviation, which is the simplest calculation, is preferably performed in step S402. The standard deviation exceeding a predetermined value is obtained by the statistical analysis on a subtraction image, as a difference between the AEC output image corresponding to the count N and the AEC output image corresponding to the count Z−1, as a result of body movement or breathing. Such a simple statistical analysis requires a relatively short calculation time, and thus is effective for prompt body movement detection for stopping the output from the radiation irradiation unit 101.

Calculation processing in steps S403, S404, or the like can be executed concurrently with the processing in step S402.

In step S403, the comparison circuit (body movement detection unit) 110 performs histogram analysis on the output subtraction image. When there is no body movement, substantially the same images are obtained. Thus, the subtraction image has an output value of substantially zero. When there is body movement, the subtraction image includes a region with an output value exceeding a predetermined value. An output value of a blank portion, in the subtraction image, including no captured image of the subject P is extremely sensitive, and thus could lead to a peculiar outlier in the histogram. Thus, whether the body movement has occurred can be determined by determining whether the calculated histogram includes such a peculiar outlier.

In step S404, the comparison circuit (body movement detection unit) 110 executes real-time edge extraction processing. More accurate body movement detection can be achieved by determining whether body movement has occurred based on a change in an edge as a result of the edge extraction processing. The edge extraction processing may not be the real time processing, and can be executed on the subtraction image after the radiography. A workflow can be improved in such a manner that the edge extraction processing is executed after the radiography and the user checking the preview image is notified of the occurrence or absence of the body movement.

As described above, the comparison circuit (body movement detection unit) 110 detects body movement of the subject P using at least one of the statistical analysis, the histogram analysis, and the edge analysis.

In step S405, the determination circuit 111 executes the threshold processing on the result of the analysis in the processing of at least one of steps S402, S403, and S404. More specifically, in step S405, an appropriate threshold is set for each analysis and whether body movement has occurred is determined. Preferably, different thresholds are set for different portions. The final determination of whether body movement has occurred is performed based on the result of the determination of each analysis. For example, the final determination that body movement has occurred can be made when body movement is detected in the analysis in at least one of steps S402, S403, and S404. Such a configuration can sensitively detect body movement, but involves a higher risk of erroneous detection.

Alternatively, the final determination that body movement has occurred can be made when body movement is found in the analysis in all of steps S402, S403, and S404. Such a configuration can detect body movement only with a limited sensitivity, but has a low risk of erroneous detection. Thus, results of the analyses are preferably optimally weighted based on the trade-off relationship between the sensitivity of body detection and the risk of erroneous detection.

Figure 5A:
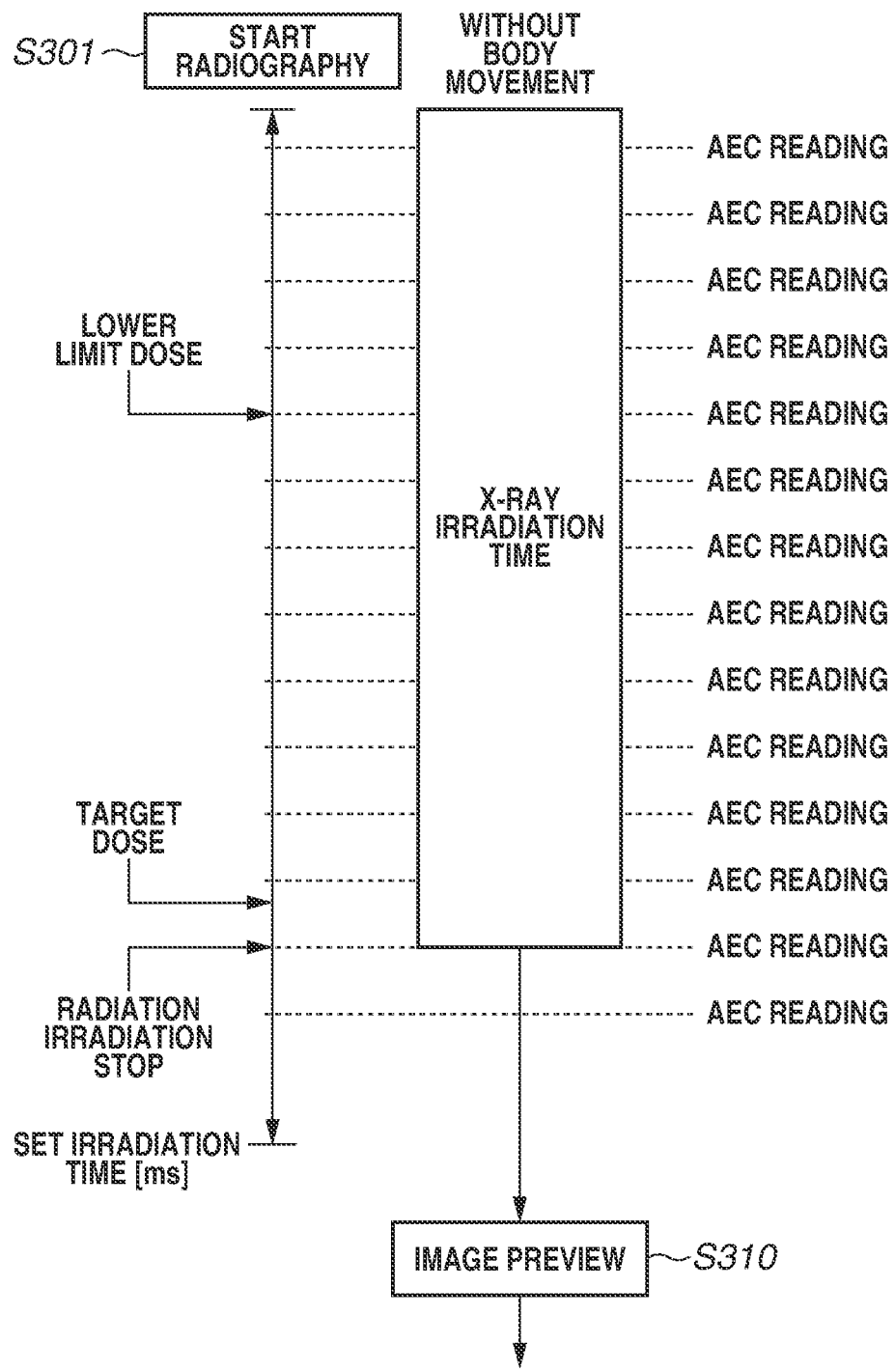
FIG. 5A is a diagram illustrating an operation of second pixels according to the first exemplary embodiment (without body movement)
Figure 5C:
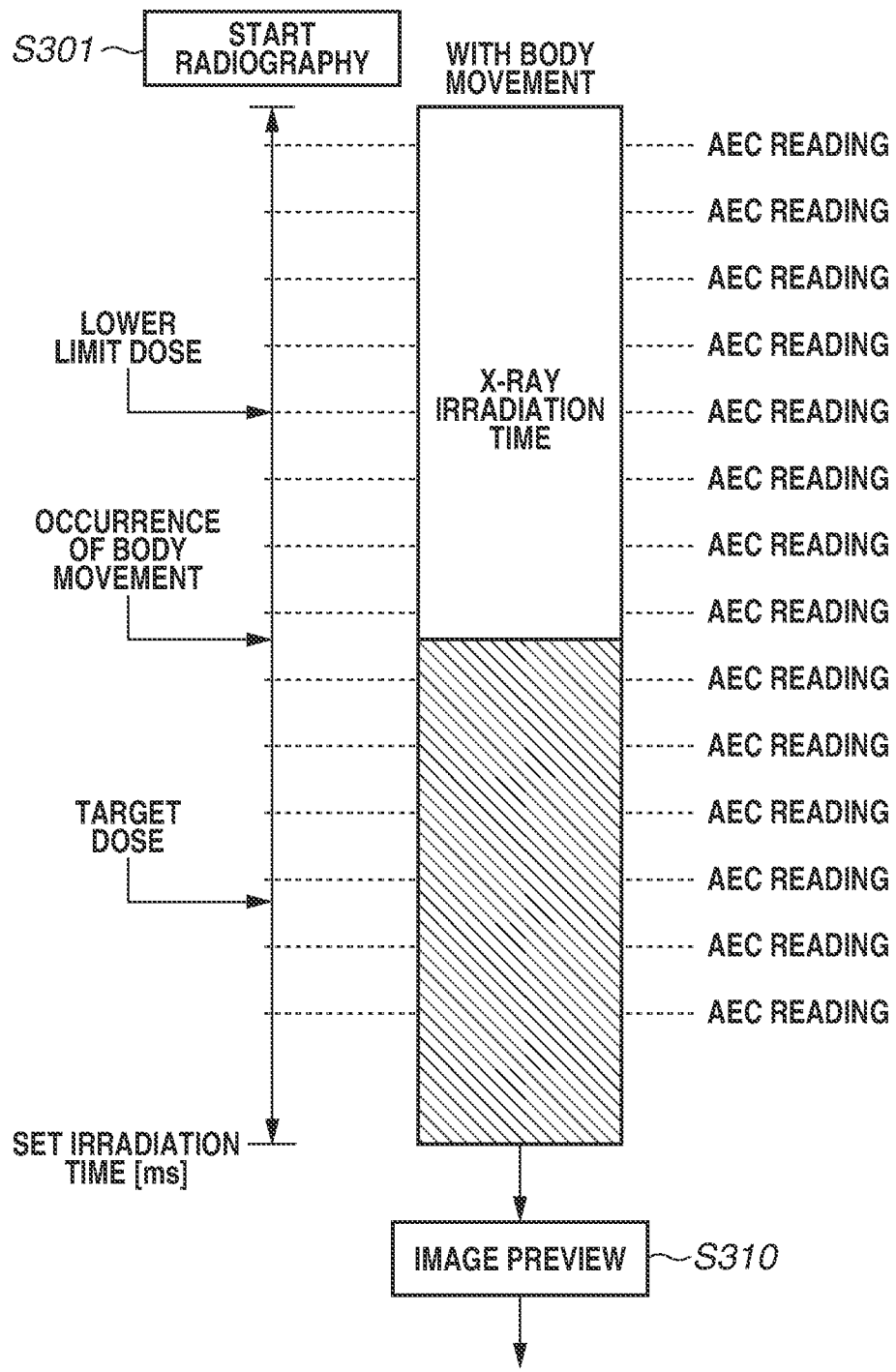
FIG. 5C is a diagram illustrating a conventional operation of second pixels (with body movement).

FIG. 5A to 5C are flowcharts illustrating processing executed in a system in cases with and without body movement. First, the case without body movement is described in FIG. 5A. As long as no body movement is detected, the radiation irradiation unit 101 keeps emitting radiation, and the AEC pixels keep outputting pixel values as detected radiation, sequentially. The radiation irradiation by the radiation irradiation unit 101 stops when the integrated value of the AEC pixel outputs (pixel values) exceeds a lower limit dose, and then exceeds the target dose. Then, the preview image is displayed (step S310). The image display (display unit) 116 displays, as a preview image, the radiographic image generated by the pre-processing circuit 105 or the image processing circuit 106.

The lower limit dose (lower limit value) is a pixel value corresponding to a minimum dose required for forming a radiographic image meeting requirement for clinical use, and is set based on a signal-to-noise (S/N) ratio and gradation. The radiographic image meeting requirement for the clinical use can be formed even if the integrated AEC pixel outputs (pixel value) do not reach the target dose, by using a technique employed for forming a high quality image with a low dose. Examples of the technique include noise reduction processing, gradation processing, or the like.

The pre-processing circuit 105 or the image processing circuit 106 functions as an image forming unit and forms a radiographic image of the subject P, when the sum of the plurality of pieces of radiographic data detected from the second pixels exceeds a predetermined lower limit value.

A radiation setting time (target time) can be set together with the target dose (target value). The radiation irradiation by the radiation irradiation unit 101 stops when the radiation setting time elapses. In other words, the radiation irradiation stopping unit 112 can stop the radiation irradiation when the radiation detection time of the second pixels exceeds a predetermined target time.

In a case where the pixel value exceeds the target dose before the set irradiation time of the radiation irradiation unit 101 elapses, the radiation irradiation stops at the timing of the AEC pixel reading in which the pixel value exceeds the target dose. In this case, the irradiation stop signal is transmitted from the radiation irradiation stopping unit 112 to the radiation control device 103 and the radiation irradiation by the radiation irradiation unit 101 stops.

Next, the case with body movement is described with reference to FIG. 5B. In FIG. 5B, the radiation irradiation by the radiation irradiation unit 101 stops after the AEC pixel outputs (the pixel value representing the dose) are integrated, the integrated AEC pixel output exceeds the lower limit dose, and then body movement is detected. The radiation irradiation stops at the timing of the AEC reading immediately after the body movement has been detected.

More specifically, in a case where the integrated value (sum) of the plurality of pieces of radiographic image data exceeds the predetermined lower limit value, and the body movement of the subject P is detected, the radiation irradiation stopping unit 112 stops the radiation irradiation before the integrated value (sum) exceeds the target value or before the detection time exceeds the target time.

In such a case, the preview image is displayed (step S310) because the integrated pixel value exceeds the lower limit dose. If the integrated pixel value does not exceed the lower limit dose when body movement is detected, a notification indicating that redoing of the radiography is required can be displayed instead of a preview image or can be displayed with a preview image obtained by image quality enhancing processing.

A conventional case with body movement is described with reference to FIG. 5C for the comparison with FIG. 5B. In FIG. 5C, even after the AEC pixel outputs (the pixel value representing the dose) are integrated, the integrated AEC pixel output (pixel value) exceeds the lower limit dose and then body movement is detected, the radiation irradiation continues until the set irradiation time elapses. Then, the preview image in which the body movement has occurred is displayed (step S310).

It can be found in a comparison between FIG. 5B and FIG. 5C that the present exemplary embodiment (FIG. 5B) can achieve a shorter radiation irradiation time after the occurrence of body movement. Thus, the present exemplary embodiment can reduce an exposure dose by stopping the radiation irradiation immediately after the body movement occurs.

In addition, by stopping the radiation irradiation immediately after the occurrence of body movement, the radiographic image can be less affected by the body movement. If the image quality degradation due to body movement can be reduced, a final output image meets a requirement for diagnosis. Thus, the radiographing does not need to be retaken. For example, in a case where the body movement occurs after the integrated pixel value exceeds the lower limit dose, the radiographic image can be formed using the integrated pixel value obtained before the occurrence of body movement. Accordingly, the final output image meeting a requirement for diagnosis can be obtained.

The radiographic system (radiographic apparatus) according to the present exemplary embodiment with the features described above can contribute to reduce exposure dose, achieve more efficient workflow for an operator, and reduce a burden on a subject.

A second exemplary embodiment of the present invention will now be described. Description of configurations, functions, and operations that are the same as those in the above-described exemplary embodiment is omitted. Differences from the above-described exemplary embodiment are mainly described.

Figure 6:
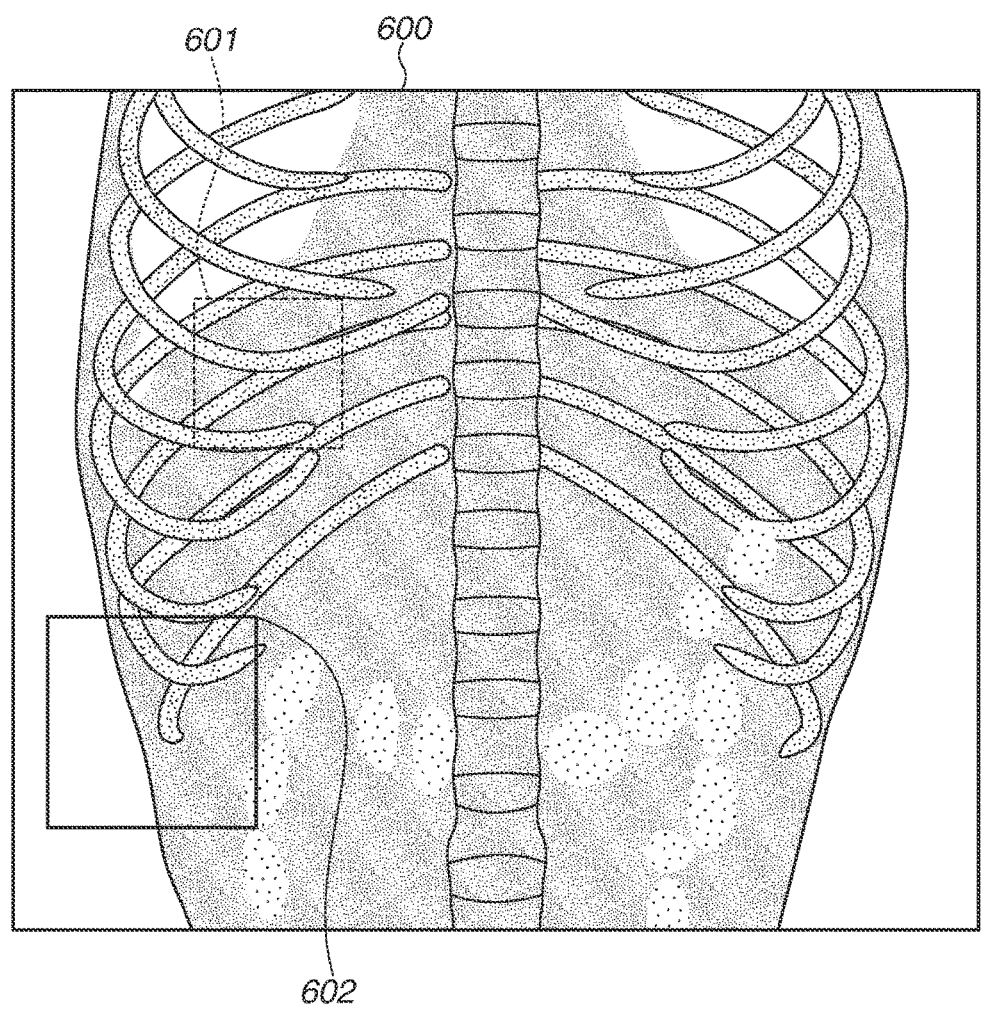
FIG. 6 is a diagram illustrating how regions of interest (ROI) are set according to a second exemplary embodiment.

FIG. 6 is a diagram illustrating an exemplary arrangement of AEC pixels according to the second exemplary embodiment. The present exemplary embodiment is different from the first exemplary embodiment in that an AEC region (first region) 601 of the AEC pixels used for the AEC and a body movement detection region (second region) 602 of the AEC pixels used for the body movement are separately set.

The radiation irradiation stopping unit 112 can stop radiation irradiation when the sum of the plurality of pieces of radiographic image data detected by the second pixels arranged in the AEC region (first region) 601 of the radiation detection unit 102 exceeds the predetermined target value. The radiation irradiation stopping unit 112 can also stop radiation irradiation when the radiation detection time of the second pixels arranged in the AEC region (first region) 601 of the radiation detection unit 102 exceeds the predetermined target time.

The comparison circuit (body movement detection unit) 110 detects body movement of the subject P by comparing the plurality of pieces of radiographic image data detected by the second pixel arranged in the body movement detection region (second region) 602 of the radiation detection unit 102 with each other.

The AEC region (first region) 601 or the body movement detection region (second region) 602 is, for example, set as an observation target of the subject P. Setting the AEC region 601 can shorten the AEC pixel reading time. Setting the body movement detection region 602 to a region suitable for the body movement detection improves accuracy of the body movement detection and shortens calculation time. For example, with the AEC pixels densely arranged in the body movement detection region 602, accuracy of the body movement detection can be improved.

When the observation target is a lung field, the body movement detection region 602 used for the body movement detection is set to the lung field. Accordingly, detail body movement detection focusing on the lung field as the observation target can be also performed.

The AEC region 601 used for the AEC and the body movement detection region 602 used for the body movement detection can be set in a fixed manner or can be set dynamically during radiography.

A processing procedure of radiography according to the second exemplary embodiment is described with reference to FIG. 7. Steps with reference numerals that are the same as those of FIG. 3 are associated with processing procedures that are the same as that in FIG. 3. The processing in steps S301 to S303 is the same as that in the first exemplary embodiment, and thus the description thereof is omitted.

In step S701, regions of interest (ROIs) extracted for setting the AEC region 601 and the body movement detection region 602 are analyzed using the AEC pixel outputs acquired in step S303.

Based on a result of the analysis, for example, the body movement detection region 602 used for the body movement detection is set to include an edge portion, such as a bodyline of the subject P. With such a setting, accuracy of the body movement detection is improved. The body movement detection region 602 including the bodyline can be set by detecting a boundary between the blank portion with no captured image of the subject P and a portion including the captured image of the subject P. Thus, the body movement detection region 602 can be appropriately set by finding a region involving a large difference between the AEC pixel outputs.

Based on a result of the analysis, for example, the body movement detection region 602 can be set to not include a body part with constant body movement, such as the heart. The body part with constant body movement, such as the heart, can be identified based on dispersion or standard deviation of pixel values varying over time.

As long as predetermined analysis speed can be achieved, i.e., as long as an analysis time sufficiently shorter than the X-ray irradiation time can be achieved, the AEC region 601 and the body movement detection region 602 can be set at appropriate positions by the ROI analysis performed with body part analysis and template matching using edge extraction.

In step S702, a setting is made in such a manner that signals are output from the AEC pixels in the AEC region 601 and the body movement detection region 602 set in step S701. Similarly to the first exemplary embodiment, the processing in steps S304 and S305 is executed concurrently with the processing in step S701.

In step S703, in a case where the AEC pixel count (N) is greater than or equal to the count (Z) and the processing in step S702 has been completed (YES in step S703), the processing proceeds to step S704. In step S704, the signals are sequentially read out from the AEC pixels in the AEC region 601 and the body movement detection region 602. In this process, an output $B_{(i,j)}$ from the AEC region 601 and an output $C_{(i,j)}$ from the body movement detection region 602 are each stored in the image storage unit 109.

The integrating circuit 107 integrates the output $B_{(i,j)}$ from the AEC region 601 one by one. In step S314, the determination circuit 111 determines whether the average of the pixels values integrated by the integrating circuit 107 has reached the target dose set by the user. A loop including steps S304, S305, and S703 includes no setting of the AEC region 601. Thus, in this process, an average value of the pixel values, which are from a certain region, integrated in the loop including steps S304, S305, and S703 is subtracted from the target dose set by the user.

In a case where the value obtained by integrating the pixel values from the AEC region 601 reaches the target dose as a result of the subtraction in step S314 (YES in step S314), the processing proceeds to step S309. In step S309, the irradiation stop signal is transmitted to the radiation control device 103, and the radiation irradiation stopping unit 112 stops the radiography.

In a case where the value has not yet reached the target dose in step S314 (NO in step S314), the processing proceeds to step S307. In step S307, the body movement detection analysis that is the same as that in the first exemplary embodiment is performed on the output $C_{(i,j)}$ from the body movement detection region 602. The output $C_{(i,j)}$ from an AEC pixel in the AEC region 601 corresponding the count Z and after is compared with the output $C_{(i,j)}$ from the AEC pixel corresponding to the count Z−1. The difference in the AEC pixel output $C_{(i,j)}$ is acquired for each pixel. Then, body movement is detected by the statistical analysis, the histogram analysis, and the edge extraction processing.

In a case where body movement is detected in steps S307 and S308 (YES in step S308), the processing proceeds to step S309, similarly to the case in which step S304 is YES. In step S309, the radiography is stopped. In a case where no body movement is detected in steps 307 and S308 (NO in step S308), the processing returns to step S704. The processing in step S310 and after are the same as those in the first exemplary embodiment, and thus the description thereof is omitted.

In the second exemplary embodiment described above, the AEC region 601 and the body movement detection region 602 are set. Accordingly, data required for the AEC and data required for body movement detection can be read out separately. Consequently, AEC pixel reading time is shortened, accuracy of the body movement detection is heightened and calculation time of the body movement detection is shortened.

In the first exemplary embodiment and the second exemplary embodiment, body movement can be detected using the AEC pixels. The optimum one of the exemplary embodiments can be selected based on their advantages. More specifically, the first exemplary embodiment is preferably employed when the body movement of the entire subject is to be detected. The second exemplary embodiment is preferably employed when the accuracy and the speed of the analysis for the body movement detection in the observation target are prioritized.

The present disclosure is also applied to processing of supplying a program for implementing the functions according to the above-described exemplary embodiments to a system or an apparatus via a network or various storage mediums, and reading and executing the program by a computer (such as a CPU or a microprocessor unit (MPU)) in the system or the apparatus.

Other Embodiments

Embodiments can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-167776, filed Aug. 30, 2016, which is hereby incorporated by reference herein in its entirety.

What is claimed is:

1. A radiographic apparatus that obtains a radiographic image of a subject, the radiographic apparatus comprising:
   a detection unit including a first pixel configured to detect radiation and a second pixel configured to detect the radiation at a frame rate higher than a frame rate of the first pixel; and
   a body movement detection unit configured to, while the subject is irradiated with the radiation, detect body movement of the subject by comparing a plurality of pieces of radiographic data detected by the second pixel with each other.

2. The radiographic apparatus according to claim 1, wherein the first pixel is configured to output radiographic data for forming the radiographic image of the subject and the second pixel is configured to output radiographic data for detecting body movement of the subject.

3. The radiographic apparatus according to claim 1, wherein the body movement detection unit is configured to detect body movement of the subject by comparing the plurality of pieces of radiation data with reference radiographic data, the reference radiographic data being a predetermined piece of the plurality of pieces of radiation data.

4. The radiographic apparatus according to claim 3, wherein the body movement detection unit is configured to determine the reference radiographic data based on radiation detection counts or a radiation detection time of the second pixel.

5. The radiographic apparatus according to claim 3, wherein the reference radiographic data is determined based on stability or fluctuation of an output from a radiation generation unit configured to generate radiation.

6. The radiographic apparatus according to claim 3, wherein the body movement detection unit is configured to detect body movement of the subject by correcting the radiographic data in such a manner that an average value of the radiographic data becomes equal to an average value of the reference radiographic data, and comparing the corrected radiographic data with the reference radiographic data.

7. The radiographic apparatus according to claim 1, wherein the body movement detection unit is configured to detect body movement of the subject by using at least one of statistical analysis, histogram analysis, and edge analysis.

8. The radiographic apparatus according to claim 1, further comprising a stopping unit configured to stop emission of the radiation when body movement of the subject is detected.

9. The radiographic apparatus according to claim 8,
   wherein the stopping unit is configured to stop the emission of the radiation in a case where a sum of the plurality of pieces of radiographic data detected by the second pixel exceeds a predetermined target value or in a case where a radiation detection time of the second pixel reaches a predetermined target time, and
   wherein in a case where body movement of the subject is detected, the emission of the radiation is stopped before the sum exceeds the predetermined target value or before the detection time reaches the predetermined target time.

10. The radiographic apparatus according to claim 8, wherein the stopping unit is configured to stop the emission of the radiation when a sum of the plurality of pieces of radiographic data detected by the second pixel arranged in a first region of the detection unit exceeds a predetermined target value or when a radiation detection time of the second pixel arranged in the first region of the detection unit reaches a predetermined target time.

11. The radiographic apparatus according to claim 1, further comprising an image forming unit configured to form the radiographic image of the subject based on the radiation detected by the detection unit.

12. The radiographic apparatus according to claim 10, wherein the image forming unit is configured to form the radiographic image of the subject when a sum of the plurality of pieces of radiographic data exceeds a predetermined lower limit value.

13. The radiographic apparatus according to claim 10, further comprising a display unit configured to display the radiographic image as a preview image.

14. The radiographic apparatus according to claim 13, wherein the first region or a second region are set as observation targets of the subject.

15. The radiographic apparatus according to claim 1, wherein the body movement detection unit is configured to detect body movement of the subject by comparing the plurality of pieces of radiographic data detected by the second pixel in a second region of the detection unit with each other.

16. The radiographic apparatus according to claim 15, wherein the second region is set to include an edge portion of the subject.

17. A radiographic system that obtains a radiographic image of a subject, the radiographic system comprising:
a radiation generation unit configured to generate radiation;
a detection unit including a first pixel configured to detect the radiation and a second pixel configured to detect the radiation at a frame rate higher than a frame rate of the first pixel; and
a body movement detection unit configured to, while the subject is irradiated with the radiation, detect body movement of the subject by comparing a plurality of pieces of radiographic data detected by the second pixel with each other.

18. A radiographic method for obtaining a radiographic image of a subject, the radiographic method comprising:
detecting radiation by a first pixel;
detecting the radiation by a second pixel at a frame rate higher than a frame rate of the first pixel; and
detecting, while the subject is irradiated with the radiation, body movement of the subject by comparing a plurality of pieces of radiographic data detected by the second pixel with each other.

19. A computer-readable storage medium storing a program for causing a computer to execute a radiographic method for obtaining a radiographic image of a subject, the radiographic method comprising:
detecting radiation by a first pixel;
detecting the radiation by a second pixel at a frame rate higher than a frame rate of the first pixel; and
detecting, while the subject is irradiated with the radiation, body movement of the subject by comparing a plurality of pieces of radiographic data detected by the second pixel with each other.

* * * * *